United States Patent [19]

Kiely et al.

[11] Patent Number: 5,312,967
[45] Date of Patent: May 17, 1994

[54] PROCESS FOR MAKING ACTIVATED ALDARATE ESTERS, ESTER/LACTONES AND LACTONES

[75] Inventors: Donald E. Kiely; Liang Chen; David W. Morton, all of Birmingham, Ala.

[73] Assignee: UAB Research Foundation, Birmingham, Ala.

[21] Appl. No.: 927,914

[22] Filed: Aug. 12, 1992

[51] Int. Cl.$^5$ .......................................... C07C 69/675
[52] U.S. Cl. ................................. 560/180; 549/305; 549/314
[58] Field of Search ................. 560/180; 549/305, 314

[56] References Cited
U.S. PATENT DOCUMENTS
4,833,230  5/1989  Kiely et al. .......................... 528/230

OTHER PUBLICATIONS

Hirasaka, et al., Chem. Pharm. Bull., 13, 677–80 (1965).
Smith, J. Chem. Soc., 633–6 (1944).
Hashimoto, et al., Makromol. Chem., Rapid Commun., 11, 393–396 (1990).

*Primary Examiner*—José G. Dees
*Assistant Examiner*—B. Frazier
*Attorney, Agent, or Firm*—Stephen Gates; Glenna Hendricks

[57] ABSTRACT

A single step process for converting aldaric acid salts to activated aldarates utilizing a lower alkanol as both solvent and esterifying agent is described. The activated aldarates are particularly useful as monomers for polymerizations with primary diamines in which the nitrogen atoms are bound to aliphatic carbon atoms to form poly(aldaramides).

6 Claims, No Drawings

PROCESS FOR MAKING ACTIVATED ALDARATE ESTERS, ESTER/LACTONES AND LACTONES

The present invention is directed to a process for preparing activated aldarate esters, ester/lactones and lactones particularly suitable for use as monomers for the preparation of poly(aldaramides).

BACKGROUND OF THE INVENTION

Kiely & Lin in U.S. Pat. No. 4,833,230 described a general method for preparing polyhydroxypolyamides from aldaric acids, and in particular poly(alkyleneglucaramides), as for example, poly(hexamethyleneglucaramide), from glucaric acid obtained from the oxidation (typically nitric acid oxidation) of glucose. Such polymers based on glucose are of particular interest because of the ready availability and low cost of glucose. The patent describes a process in which the calcium salt of glucaric acid is converted with the acid form of a cation exchange resin to a mixture of forms of glucaric acid in aqueous solution. [Hirasaka et al, Chem. Pharm. Bull., 13, (1965) reported that glucaric acid in aqueous solution can exist as the diacid, acid/lactone and dilactone.] Water is removed from the mixture, which without separation is then esterified with acid catalyst and an alkanol. The esterified glucaric acids, hereinafter described as "activated glucarates", without separation are then polymerized with primary diamines to yield poly(alkyleneglucaramides). In summary, the Kiely & Lin patent describes a two step conversion of a salt of glucaric acid to activated glucarates. The first step converts glucaric acid salt to a mixture of glucaric acid forms using the acid form of an ion-exchange resin and water as solvent. The water is then removed by a distillation (evaporation) process. The second step involves conversion of the mixture of glucaric acid forms to a mixture of activated glucarates with acid in alkanol. The activated glucarates then are used as monomers for polymerization with appropriate aliphatic diamines in the presence of a tertiary amine to form poly(alkyleneglucaramides).

Smith, J. Chem. Soc., 632 (1944), had previously prepared these glucaric acid lactones by neutralization of potassium acid glucarate with aqueous sulfuric acid and similarly removing the water before esterification.

More recently Hashimoto et al., Makromol. Chem., Rapid Commun., 11, 393 (1990), have described the preparation of a poly(aralkyleneglucaramide), poly(p-xylyleneglucaramide), a type of polyhydroxypolyamide based upon the aralkylenediamine p-xylylenediamine as the diamine monomer using a specific activated glucarate (a dilactone), D-glucaro-1,4:6,3-dilactone, which had been prepared in a similar fashion from an aqueous solution of potassium acid glucarate as the glucarate monomer.

SUMMARY OF THE INVENTION

In accordance with this invention a single step process has been found for converting aldaric acid salts to activated aldarates utilizing a lower alkanol as both solvent and esterifying agent. The activated aldarates are particularly useful as monomers for polymerizations with primary diamines in which the nitrogen atoms are bound to aliphatic carbon atoms to form poly(aldaramides). Because of the well-known difficulty of preparing pure solid glucaric acid (I) in a weighable form, the process is particularly useful for converting glucaric acid

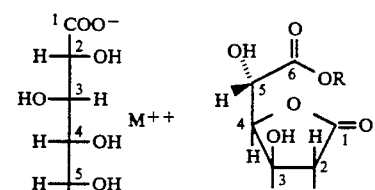

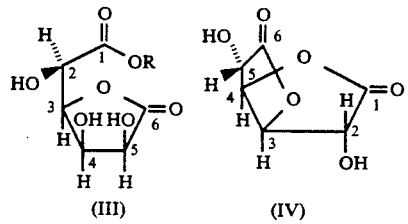

alkali metal or ammonium salts (Ia where $A^+$ is $Na^+$, $K^+$, or $NH_4^+$) in particular the readily available monopotassium acid glucarate, to activated glucarates useful for polymerization with diamines to form poly(glucaramides), i.e. polyhydroxypolyamides based upon glucose, without the need to separate the activated glucarate monomers.

In accordance with another embodiment of this invention a single step process has been found for converting an aldaric acid, in particular a glucaric acid salt, in the substantial absence of water to single, solid, easily weighable, activated aldarate forms (ester/lactoes II and III or dilactone IV) by using a lower alkanol as both solvent and esterifying agent. Use of these individual activated aldarates as monomers affords superior stoichiometric control in polymerizations with diamines to form polyhydroxypolyamides.

Still another embodiment of the invention is a process for converting crystalline forms of glucaric acid with alkanol/acid to give a mixture of activated glucarates which can be used directly as monomers in condensation polymerizations.

DETAILED DESCRIPTION OF THE INVENTION

In one embodiment of the invention an alkali metal or ammonium glucararic acid salt such as potassium acid glucarate (Ia $A^+=K^+$) is converted in a single direct step to a mixture of activated glucarates using acid in an alkanol in the substantial absence of water. (The use of the name glucaric acid and derivatives or polymers derived from glucaric acid most often refers to D-glucaric acid; the acid, derivatives and polymers thereof derived from the natural and most abundant form of glucose, i.e. D-glucose. However, the methods described herein are equally applicable to L-glucaric acid and its derivatives). The process of the invention accomplishes this conversion of glucaric acid salt to activated glucarates in one step without using water as a solvent so that no energy-intensive removal of water is required. The general method used for the conversion of a salt of glucaric acid, in particular the half potassium salt of glucaric acid is as follows: the glucaric acid salt is stirred with an alkanol in the presence of a strong acid, preferably an alkanol containing dissolved hydrogen chloride or a strong acid ion exchange resin, until dissolution/esterification of the salt is complete. The insoluble inorganic salt formed in the dissolution/esterification process or the salt-containing ion exchange resin is removed by means such as filtration, centrifugation, decantation or the like and then excess alkanol may be removed by distillation or equivalent means if desired. The residue recovered from this single step process is a mixture of activated glucarates that may be used directly for polymerization with appropriate diamines, optionally with additional minor amounts of tri- or higher polyamines, without the need for first separating the component activated glucarates.

Another embodiment of the invention takes advantage of direct and efficient crystallization of specific activated glucarates (ester/lactones) after removal of inorganic salt when alkanol/HCl (or other alkanol/acid combination) is used in the glucaric acid salt dissolution/esterification process. The presence of excess alkanol will not interfere with use of the solution as a monomer. If it is desired for polymerization or some other use of the aldarate, concentration of the alkanol solution of activated glucarates by evaporation means such as distillation or other means for evaporation of the alkanol well-known to the art leads to formation of readily crystallized ester/lactones, specific activated aldarates, which are easily separated from the residual mixture by filtration, decantation or other means well-known in the art. That is, the single step process for converting a glucaric acid salt to polymerizable mixtures of activated glucarates can also be employed to produce single, crystalline and weighable amounts of an activated glucarate for use in the polymerization process. When the alkanol employed in the process is methanol, crystalline methyl D-glucarate 1,4-lactone (II, R is methyl) is conveniently obtained in yields of 58% or more as a weighable, single activated glucarate which can be employed for direct use in polymerizations. When the alkanol employed in the process is ethanol, crystalline ethyl D-glucarate 6,3-lactone (III, R is ethyl) suitable for direct use in polymerizations is obtained.

In still another embodiment of the invention the 1,4-lactone and the 6,3-lactone may also be prepared directly employing a strong acid cation exchange resin in place of the dissolved hydrogen chloride or other dissolved strong acid. Typically the 1,4-lactone is formed in yields of 70% or more and the 6,3-lactone in yields of 60% or more, as solid materials. A possible drawback to this method is that it is possible for a significant amount of product to be held up on the resin, thus reducing the yield of lactone.

When either of the procedures above is used the residual mixture of activated glucarates remaining after crystallization of the lactones can be retained for use in polymerization or treated again (re-equilibrated) with alkanol and acid to obtain more of the specific crystalline activated glucarate.

In still another embodiment of the invention a crystalline form of glucaric acid, D-glucaro-6,3-lactone (III, R is H), is reacted with alkanol/acid, to yield a mixture of activated glucarates that can be used directly as monomer(s). This method may also be employed with the other less readily available form of D-glucaric acid, D-glucaro-1,4-lactone (II, R is H).

The processes of the invention may utilize any lower aliphatic alcohol such as methanol, ethanol, propanol, isopropanol, butanol, isobutanol, etc., but in general the preferred alkanols are methanol or ethanol, which are inexpensive and are more easily removed from the products.

Primary diamines and polyamines suitable for use in practice of the invention are amines in which the nitrogen atoms are bound to aliphatic carbon atoms. Diamines include hydrocarbylenediamines and heterohydrocarbylenediamines. The hydrocarbylenediamines are alkylene and aralkylene diamines having the general formula $H_2NC_{n'}R_{2n'}—(R')_n—C_{n'}R_{2n'}NH_2$, wherein each R is individually selected from the group comprising hydrogen, alkyl, alkenyl, aryl, aryl-substituted alkyl and alkenyl, and alkyl- and alkenyl-substituted aryl;

R' is selected from the group comprising alkylene, alkenylene, aryl- and alkyl-substituted alkylene and alkenylene, arylene, alkyl- and alkenyl-substituted arylene;

n is zero or 1; and each n' has a value of at least 1.

The heterohydrocarbylenediamines are diamines having the general formula $H_2NC_{n'}R_{2n'}—(R'HR'')_{n'''}—C_{n'}R_{2n'}NH_2$, wherein R, R' and n' are designated as above;

each R'' is individually R' or a valence bond;

H is selected from the group comprising —O—, —S—, —NR'''— and —PR'''—, wherein R''' is selected from the group comprising hydrogen, alkyl, alkenyl, aryl, aralkyl and alkaryl; and n''' may be 0 or an integer.

Examples of diamines include but are not limited to: alkylenediamines such as ethylenediamine, hexamethylenediamine, 2-methylpentamethylenediamine, 2-phenyltetramethylenediamine and the like; aralkyldiamines such as o-, m- and p-xylylenediamine, ar-alkyl substituted xylylenediamines and the like; and heteroalkylene diamines such as polyoxyethylenediamine, polyoxypropylene diamine, 4-aza-4-octylheptamethylenediamine, 4-phospha-4-ethylheptamethylenediamine, polythioethylenediamine and the like.

Examples of hydrocarbylenediamines include but are not limited to: alkylenediamines such as ethylenediamine, hexamethylenediamine, 2-methylpentamethylenediamine, 2-phenyltetramethylenediamine and the like; aralkyldiamines such as o-, m- and p-xylylenediamine, ar-alkyl substituted xylylenediamines and the like. Heterohydrocarbylenediamines include but are not limited to polyoxyethylenediamines, polyoxypropylenediamines, 4-aza-4-octylheptamethylenediamine, 4-phospha-4-ethylheptamethylenediamine, polythioethylenediamines and the like. Minor amounts of higher functionality primary amines may be added to introduce branching in the polymer. Useful higher functionality amines include but are not limited to the polyoxypropylenetriamines (Jeffamine T403, sold by Texaco is an example) and tetrakis(aminomethyl)methane. Care must be taken to avoid adding so much higher functionality that gelation of the polymer will occur. The amount needed to obtain the desired degree of branching may be determined by routine experimentation.

The process of the invention provides several significant improvements to the methods previously employed in the art including the following:

a. the use of a single alkanol as solvent and as esterifying alkanol eliminates the use of water in the process, the added energy requirements and associated costs of water removal and the well-known difficulty of recovering solid aldaric acid derivatives from aqueous media. The ability to carry out the conversion of glucaric acid salt to polymers on an industrial scale without the energy requirements and associated costs of water removal as an added step at any stage of the process and the greater ease of recovering the products in a solid form when desired are significant improvements;

b. good stoichiometric control of the mixture of unseparated monomeric activated glucarates is ensured as the mixture of activated glucarates formed in the acid-/alkanol solution is the same molar amount as the starting glucaric acid salt. The molar amount of the latter is determined by using a weighed amount of solid glucaric acid salt of known composition. If the ionexchange resin method is not used for the esterification step, there of course is no possibility that activated glucarates can be retained by the resin. When the preferred dissolved hydrogen chloride is used in the process, insoluble inorganic salts are readily separated (in particular potassium chloride when using potassium acid glucarate as the starting salt) and the alkanol solution contains the same molar amount of a mixture of activated glucarates as of glucaric acid salt initially employed;

c. the process allows for direct and efficient formation of specific, crystalline, weighable, easy to handle and process, activated glucarates (ester/lactones) that can be used directly with good stoichiometric control as the activated glucarate monomer for polymerizations. The importance of controlling stoichiometry in a copolymerization process to obtain high polymer is well understood in the art. Use of these crystalline activated glucarates or mixtures of activated glucarates as described above confers significant advantages in more precise stoichiometric control for high polymer formation;

d. the availability of ethyl D-glucarate 6,3-lactone for use in polymerizations offers the advantage of employing an alkanol which would be acceptable if it were (inadvertently) carried over into products intended for direct human use. Ethanol is a food acceptable alkanol, is found in a variety of food products, and of course is the potable alcohol of alcoholic beverages; and e. the availability of specific D-glucaric acid-lactones, D-glucaro-1,4-lactone or D-glucaro-6,3-lactone, as direct precursors for conversion to a mixture of activated glucarates in alkanol/acid suitable for polymerization is of advantage when a process for isolating them from a D-glucaric acid preparation is convenient and/or economically advantageous.

EXPERIMENTAL

General methods. All $^1$H and $^{13}$C NMR were recorded with a GE 300WB FT-NMR spectrometer at 300.13 MHz and 75.4 MHz. Chemical shifts are reported as ppm (δ) downfield from tetramethylsilane (TMS) or 2,2,3,3-tetradeuterio-3-trimethylsilyl propionate (TSP). IR spectra were recorded with a Nicolet IR42 FT IR spectrometer, as KBr pellets. All solvents used were reagent grade unless stated otherwise. Melting points were recorded with Fisher-Johns Melting Point Apparatus and are reported uncorrected. Solvent evaporations were carried out in vacuo. Methanol-diamine solutions were standardized by diluting an aliquot of the solution with water and titrating with standardized hydrochloric acid using a pH meter as a monitor to obtain a titration curve and determining the end point from the curve.

The following examples are provided to demonstrate the present invention. Because the examples are for illustrative purposes only, the invention should not be limited thereby.

EXAMPLE 1

Preparation of a mixture of activated D-glucarates in a single step process from a salt of D-glucaric acid and alkanol which is suitable for direct use in polymerization with hexamethylenediamine to give poly(hexamethylene-D-glucaramide).

For convenient preparation of a methanolic solution of HCl, acetyl chloride (3.00 mL, 42 mmol, Aldrich) was added dropwise to methanol (25 mL) in a 250 mL round-bottomed flask cooled in an ice bath. Monopotassium D-glucarate (5.000 g, 20.15 mmol) was added to the cold MeOH/HCl solution, the mixture was refluxed in an oil bath for 3–4 h, cooled to room temperature and the white solid (KCl) was removed by filtration and dried: yield KCl 1.346 g (90.6%). The filtrate was concentrated at 65° C. to yield a syrup which was dissolved in methanol (15 mL) to give a clear solution of methanol esterified D-glucaric acid. This procedure was repeated to form a total of four identical solutions each of which were evaluated for their suitability as monomer for the preparation of poly(hexamethylene-D-glucaramide) using one of Methods A–D below. A fifth method (Method E) was used to evaluate ethanol esterified D-glucaric acid.

A) Triethylamine method. Triethylamine was added to the solution of methanol esterified D-glucaric acid until the solution became basic (pH paper) and then additional triethylamine (1.0 mL) was added. A methanol solution of 1.139 M hexamethylenediamine (17.7 mL, 20.16 mmol) then was added to the above solution and within 15 min a large amount of white solid was produced. The reaction was stirred at room temperature for 3 h, the white solid was removed by filtration, washed with methanol (3×10 mL), acetone (3×10 mL) and dried at reduced pressure (0.25 torr) at 75° C. for 6 h to yield poly(hexamethylene-D-glucaramide) (5.475 g, 18.86 mmol, 93.6%), based upon comparison ($^1$H NMR and IR) with authentic material.

B) Sodium carbonate method. Sodium carbonate (1.0 g, 9.43 mmol) was added to the solution of methanol esterified D-glucaric acid and if carbon dioxide gas evolved, more sodium carbonate was added until gas evolution stopped and the solution became neutral (pH paper). The white solid formed (NaCl) was removed by filtration and triethylamine (1.0 mL) was added to the filtrate and then a methanol solution of 1.139 M hexamethylenediamine (17.7 mL, 20.16 mmol). The reaction mixture was stirred at room temperature for 3 h, solid being formed within the first 10 min. The solid was removed by filtration, washed with methanol (3×10 mL), acetone (3×10 mL) and dried overnight to yield poly(hexamethylene-D-glucaramide) (5.205 g, 17.93 mmol, 88.97%) based upon comparison ($^1$H NMR and IR) with authentic material.

C) Anion resin method. Hydroxide form anion exchange resin (10 mL, 14 mmol of total OH. exchange capacity, Dowex 1-X8, Anion Exchange Resin, pretreated with 1.0 N NaOH solution and methanol, Bio*-Rad Laboratories,) was added to the solution of methanol esterified D-glucaric acid. The mixture was stirred at room temperature for 3 h and the resin was removed by filtration. Triethylamine was added to the filtrate until the solution was just basic (pH paper), and then additional triethylamine (1.0 mL), and a methanol solution of 1.139 M hexamethylenediamine (17.7 mL, 20.16 mmol) were added. The reaction mixture was stirred at room temperature for 3 h, an insoluble solid forming within the first 15 min. The white solid was removed by filtration, washed with methanol (3×10 mL), acetone (3×10 mL) and dried for 12 h to yield poly(hexamethylene-D-glucaramide) (3.480 g, 11.99 mmol, 59.5%) based upon comparison ($^1$H NMR and IR) with authentic material.

D) Sodium methoxide method. Solid sodium methoxide was added to the solution of methanol esterified D-glucaric acid until the solution became neutral (pH paper). The insoluble white solid (NaCl) was removed by filtration and triethylamine (1.o mL) was added to the filtrate and then a methanol solution of 1.139 M hexamethylenediamine 17.7 mL, 20.16 mmol). The reaction mixture was stirred at room temperature for 3 h, an insoluble white solid being formed within 15 min. The white solid was filtered, washed with methanol (3×10 mL) and acetone (3×10 mL) and dried to yield poly(hexamethylene-D-glucaramide) (5.104 g, 17.58 mmol, 87.24%) based upon comparison ($^1$H NMR and IR) with authentic material.

E) Ethanol - sodium methoxide method. Monopotassium D-glucarate (5.000 g, 20.15 mmol) was treated with ethanol/HCl (prepared by adding 3 mL acetyl chloride to 25 mL ethanol) to obtain an ethanol esterified D-glucaric acid solution. Solid KCl precipitated from this esterification reaction mixture more efficiently (95.94%) than when methanol was used in the esterification (90.6%). Concentration of this ethanol esterified glucaric acid solution gave a syrup which was dissolved in methanol and neutralized with sodium methoxide. No insoluble NaCl was observed to be formed during the neutralization. Addition of triethylamine (1.0 mL) and a methanol solution of 1.139 M hexamethylenediamine (17.7 mL, 20.16 mmol) to the solution caused precipitation of polyamide within 10 min. The mixture was stirred at room temperature for 3 h, the white solid was removed by filtration, washed with methanol (3×10 mL), acetone (3×10 mL) and dried to yield poly(hexamethylene-D-glucaramide) (5.302 g, 18.26 mmol, 90.16%) based upon comparison ($^1$H NMR and IR) with authentic material.

EXAMPLE 2

Preparation of methyl D-glucarate 1,4-lactone.

Method A (from monopotassium D-glucarate): The acid form of a cation exchange resin (REXYN 101(H), Fisher) was washed with methanol until the washings were colorless. Methanol (200 mL), the above treated resin (105 mL) and monopotassium D-glucarate (D-saccharic acid monopotassium salt, 50.0 g, 201.5 mmol) were added successively to a 1000 mL Erlenmeyer flask. The flask was sealed, placed in a shaker/water bath (Precision Scientific Co.) at a water bath temperature of 50° C. and was shaken until the white saccharic acid salt was completely dissolved (about 3 h). The resin was removed by filtration, washed with methanol (2×15 mL) and retained for regeneration to its acid form. The combined filtrate and washings were transferred to a 500 mL round-bottomed flask and concentrated to a thick syrup. The syrup, seeded with pure methyl D-glucarate 1,4-lactone, solidified at room temperature in two-three days. The solid cake was dried further at room temperature (0.25 torr) for 36 h to give a slightly yellow solid (29.4 g, 143 mmol, 71.5%) which could be used directly for polymerization. Triturating the crude solid at room temperature with ethanol gave a white solid which was separated by filtration and dried at reduced pressure (0.25 torr) and 65° C. for 12 h: yield of purified methyl D-glucarate 1,4-lactone, 20.89 g (101.3 mmol, 50.8%): mp 158°–160° C. (lit. 165° C.; Smith, *J. Chem. Soc.*, 632 (1944)); IR (KBr) 3400 cm$^{-1}$ (O—H, stretch), 1781 cm$^{-1}$ (five membered lactone C=O), 1728 cm$^{-1}$ (ester C=O); $^1$H NMR (CD$_3$OD) δ 4.97 (dd, 1H, H-4, $J_{4,5}$=2.36 Hz), 4.60 (d, 1H, H-2, $J_{2,3}$=8.15 Hz), 4.49 (d, 1H, H-5), 4.44 (dd, 1H, H-3, $J_{3,4}$=7.31 Hz), 3.73(s, 3H, —CH$_3$).

Anal. Calcd for C$_7$H$_{10}$O$_7$ (206.15): C, 40.79; H, 4.89. Found : C, 40.54; H, 4.92.

Method B (from monopotassium D-glucarate): Monopotassium D-glucarate (20.00 g, 80.61 mmol) was added to a 250 mL round-bottomed flask containing methanol (100 mL). A solution of methanolic HCl prepared by careful addition of acetyl chloride (20 mL, 276 mmol, 98%, Aldrich) to methanol (25 mL) kept at ice bath temperature was added to the mixture. The reaction mixture was refluxed for 3–4 h, an insoluble white solid being observed in the reaction vessel during the entire refluxing time. The solid was separated by filtration and dried in a vacuum oven for 12 h at 70° C. The melting point of the solid was greater than 250° C. and the solid gave no $^1$H NMR signal (D$_2$O), properties consistent with KCl, the inorganic by-product from the reaction; yield 5.386 g (72.24 mmol, 89.62%). The filtrate was concentrated at 50° C. to give a syrup which was seeded with pure methyl D-glucarate 1,4-lactone. The syrup, when kept at room temperature, solidified and was dried at reduced pressure (0.25 torr) for 24 h to complete the crystallization: yield of crude solid methyl D-glucarate 1,4-lactone, 16.52 g. The combined weight of solid KCl and solid methyl D-glucarate 1,4-lactone was 21.91 g (96.80% of theoretical). The $^1$H NMR and IR spectra of solid methyl D-glucarate 1,4-lactone prepared by Method A and Method B were identical. Elemental analysis of methyl D-glucarate 1,4-lactone prepared by method B indicated the presence of potassium chloride (~ 6% by weight) in the sample. The residual inorganic salt was removed in the following way. H$^+$ form cation exchange resin (10 mL) was added to solid methyl D-glucarate 1,4-lactone (16.52 g) which had been dissolved in methanol (50 mL). The mixture was stirred at room temperature (3 h) and the resin was removed by filtration. The filtrate was concentrated to a syrup which solidified spontaneously. The solid was triturated with acetone, separated by filtration and dried in a vacuum oven at 70° C. for 8 h to give methyl D-glucarate 1,4-lactone (9.79 g, 47.47 mmol, 58.89%), identical ($^1$H NMR, IR) to that obtained from Method A.

Anal. Calcd for C$_7$H$_{10}$O$_7$ (206.15): C, 40.79; H, 4.89. Found: C, 39.79: H, 4.89: K, 0.00.

EXAMPLE 3

The suitability of the methyl D-glucarate 1,4-lactone prepared in Example 2 as a monomer was determined by using it to prepare poly(ethylene-D-glucaramide). Triethylamine (0.5 mL) was added to a methanol (20 mL) solution of methyl D-glucarate 1,4-lactone (2.000 g, 9.702 mmol) and then a methanol solution of 0.476M ethylenediamine (20.38 mL, 9.701 mmol, 1:1 molar ratio of diamine to lactone, Eastman Kodak). Addition of the diamine solution to the solution of the lactone immediately produced a clear light yellow solution which became cloudy upon stirring at room temperature for 30 min. The polymerization mixture was kept at room temperature with stirring and after 48 h, a solid was removed by filtration. The solid was suspended in methanol (40 mL) and refluxed for 4 h. The solid was removed by filtration, and dried at 60° C. at reduced pressure (0.25 torr) to give water soluble poly(ethylene-D-glucaramide) (2.12 g, 9.05 mmol, 93.3%): mp 185° C.; IR (KBr) 3346 cm$^{-1}$ (O—H, stretch), 2935 cm$^{-1}$ (C—H stretch), 1646 cm$^{-1}$ (Amide I, C=O stretch), 1546 cm$^{-1}$ (Amide II, N—H bending); $^1$H NMR (D$_2$O) δ 4.351 (d, 1H, H-2, $J_{2,3}=1.38$ Hz), 4.113 (t, 1H, H-3, $J_{3,4}=4.36$ Hz), 3.976 (t, 1H, H-4, $J_{4,5}=5.08$ Hz), 4.263 (d, 1H, H-5), 3.44 (s, 4H, H-1' and H-2').

Anal. Calcd for [C$_8$H$_{14}$N$_2$O$_6$]$_6$: C, 41.03; H, 6.02; N, 11.96. Found: C, 40.97; H, 6.36; N, 11.53.

EXAMPLE 4

Preparation of ethyl D-glucarate 6,3-lactone. Acid form cation exchange resin (110 mL, REXYN 101(H), Fisher) was washed with ethanol until the washings were colorless. The ethanol washed resin, monopotassium D-glucarate (50.00 g, 201.5 mmol, Sigma) and ethanol (200 mL) were added to a 1000 mL Erlenmeyer flask. The flask was sealed and put in a shaker/water bath at 55° C. for 4 h or until the white solid was dissolved. The resin was removed by filtration and washed with ethanol (3×10 mL) and the combined filtrate and washings were concentrated to give a thick syrup. The syrup was seeded with ethyl D-glucarate 6,3-lactone and kept for two-three days at room temperature by which time most of the syrup solidified. The sticky cake was then kept under vacuum (0.25 torr) for three days at room temperature to yield solid and slightly yellow crude ethyl D-glucarate 6,3-lactone (26.81 g, 121.8 mmol, 60.45%). Trituration of this solid with acetone followed by filtration gave a white solid product. The acetone filtrate was concentrated and the resulting solid triturated and separated as above. The combined white solids were dried in a vacuum oven at 55° C. for 6 h to give ethyl D-glucarate 6,3-lactone (25.83 g, 117.3 mmol, 58.2%): mp 121°-123° C. (lit. 122° C.; Zinner and Fischer, Chem. Ber., 89, 1503 (1956)); IR (KBr), 1774 cm$^{-1}$ (C=O stretch, five membered lactone) and 1717 cm$^{-1}$ (C=O stretch, ester); $^1$H NMR (D$_2$O) δ 1.10 (t, 3H, O—CH$_2$CH$_2$H$_3$), 4.45-4.60 (m, 4H, H-2, H-3, H-4, H-5); The unresolved portion of the spectrum (H-2, H-3, H-4, H-5) was very similar to that from the corresponding acid: D-glucaro-6,3-lactone; $^{13}$C NMR (D$_2$O) δ 178.8 (lactone C=O), 172.8 (ester C=O), 81.6 (C-3), 71.6 (C-5), 71.3 (C-2) and 70.2 (C-4), 64.3 (O—CH$_2$CH$_3$), 14.4 (O—CH$_2$CH$_3$).

Anal. Calcd for C$_8$H$_{12}$O$_7$·(H$_2$O)$_{0.5}$: C, 41.93; H, 5.72. Found: C, 42.01; H, 5.10.

EXAMPLE 5

The suitability of the ethyl D-glucarate 6,3-lactone prepared in Example 4 as a monomer was determined by using it to prepare poly(hexamethylene-D-glucaramide). Triethylamine (0.5 mL) was added to a methanol (40 mL) solution of ethyl D-glucarate 6,3-lactone (1.000 g, 4.36 mmol) and then a methanol solution of 1.139 M hexamethylenediamine (3.73 mL, 4.25 mmol, 1.00:1.03 molar ratio of diamine to lactone, Aldrich). The colorless solution was stirred at room temperature and within the first 5-10 min a considerable amount of white precipitate was observed. The mixture was stirred at room temperature for 48 h, the solid was removed by filtration, washed with methanol (2×15 mL), acetone (2×15 mL) and dried at reduced pressure (0.25 torr) at 75° C. for 36 h to give poly(hexamethylene-D-glucaramide) (1.014g 3.49 mmol, 80.0%): mp 192°-194° C. (dec.) (lit. mp 190°-205° C.; U.S. Pat. No. 4,833,230); IR (KBr) 3306 cm$^{-1}$(O—H, stretch), 2931 cm$^{-1}$(C—H, stretch), 1641 cm$^{-1}$ (Amide I, C=O), 1545 cm$^{-1}$ (Amide II, N—H); $^1$H NMR (CF$_3$COOD) δ 4.92 (d, 1H, H-2, $J_{2,3}=2.77$ Hz), 4.74 (broad s, 1H, H-3), 4.57 (t, 1H, H-4, $J_{4,5}=6.17$ Hz), 4.87 (d, 1H, H-5), 3.53 (d, 4H, H-1' and H-6'), 1.78 (s, 4H, H-2' and H-5'), 1.50 (s, 4H, H-3' and H-4').

Anal. Calcd for [C$_{12}$H$_{22}$N$_2$O$_6$]$_n$: C, 49.65; H, 7.64; N, 9.65. Found : C, 49.42: H, 7.82: N, 9.51.

EXAMPLE 6

Preparation of an oxygen-hetero-poly(alkylenealdaramide), poly(3',6'-dioxaoctamethylene-D-glucaramide).

Triethylamine (0.5 mL) and a methanol solution of 1.631 M 3,6-dioxaoctamethylenediamine (triethyleneglycoldiamine, EDR 148, 6.24 mL, 10.2 mmol, 1.05:1 molar ratio of diamine to lactone, Texaco) was added to a methanol (40 mL) solution of methyl D-glucarate 1,4-lactone (2.000 g, 9.70 mmol). The colorless solution was stirred at room temperature and within 30 min, a precipitate began to form. The initial precipitate had an oily consistency and stuck to the walls of the reaction flask, but over time with stirring, the oil solidified and could be easily scraped from the wall of the reaction flask. Because the precipitation process was slow, stirring was normally allowed to continue for 48 h before the solid was removed. The white solid product was dried at a reduced pressure (0.25 torr) at 75 ° C. for 36 h to give poly(3',6,-dioxaoctamethylene-D-glucaramide), yield 1.944 g (6.03 mmol, 62.2%); mp softened at 110 ° C. and completely liquified by 150 ° C.; IR (KBr) 3309 cm$^{-1}$(O—H, stretch), 2876 cm$^{-1}$(C—H, stretch), 1645 cm$^{-1}$ (Amide I, C=O), 1542 cm$^{-1}$ (Amide II, N—H stretch); $^1$H NMR (D$_2$O) δ 4.351 (d, 1H, H-2, $J_{2,3}=2.31$ Hz), 4.116 (t, 1H, H-3, $J_{3,4}=4.55$ Hz), 3.979 (t, 1H, H-4, $J_{4,5}=5.16$ Hz), 4.274 (d, 1H, H-5), 3.702 (s, 4H, —O—CH$_2$—CH$_2$—O—), 3.669 (t, 4H, N—C—CH$_2$—O—), 3.474 (broad s, 4H, —NH—CH$_2$—), 2.915 (t, —CH$_2$NH$_2$).

Anal. Calcd for [C$_{12}$H$_{22}$N$_2$O$_8$]$_n$: C, 44.72; H, 6.88; N, 8.69. Found : C, 44.05; H, 6.98; N, 8.28.

EXAMPLE 7

Polymerization employing more than one activated aldarate; e.g. methanol esterified xylaric acid and ethyl D-glucarate 6,3-lactone with hexamethylenediamine, poly(hexamethylene-D-glucaramide-xylaramide).

Ethyl glucarate 6,3-lactone (260 mg, 1.25 mmol), 9.4 mL methanol esterified xylaric acid in methanol (0.4 mmol/mL, 3.76 mmol), hexamethylenediamine (1.139 M in methanol, 4.4 mL, 5.00 mmol) and triethylamine (0.70 mL, 5.0 mmol) were added to methanol (30 mL). The reaction was stirred for 24 h at room temperature, the precipitate filtered, washed with methanol (2×10 mL) and dried under vacuum to give 1.10 g (82.0%) of light tan powder: mp 185° C. (d). IR (KBr) 3312 cm$^{-1}$ (O—H and N—H stretch), 2932 and 2857 cm$^{-1}$(C—H stretch), 1647 cm$^{-1}$ (amide I, C=O stretch), 1543 cm$^{-1}$ (amide II, N—H bend)

Analysis—found C, 49.36; H, 7.76; N 10.27. This has been calculated as corresponding to an approximate composition $\{[C_{12}H_{22}N_2O_6]_3/[C_{11}H_{20}N_2O_5]\}_n$: which would have the analysis C, 49.74; H, 7.65; N, 9.83.

EXAMPLE 8

Polymerization employing more than one aldarate and more than one diamine; methanol esterified xylaric acid and ethyl D-glucarate 6,3-lactone with hexamethylenediamine and dodecamethylenediamine as the amines, poly(hexamethylenedodecamethylene-D-glucaramide-xylaramide). Ethyl glucarate 6,3-lactone (520 mg, 2.50 mmol), 6.25 mL methanol esterified xylaric acid in methanol (0.4 mmol/mL, 2.50 mmol), a methanol solution of hexamethylenediamine, 1.139 M (2.2 mL, 2.50 mmol), dodecamethylenediamine (500 mg, 2.50 mmol) and triethylamine (0.70 mL, 5.0 mmol) were added to methanol (37.4 mL). The reaction was stirred for 24 h at room temperature, the precipitate filtered, washed with fresh methanol (2×10 mL) and dried under vacuum to give 1.20 g (75.6%) of a tan powder: mp 145° C. IR (KBr) 3297 cm$^{-1}$ (O—H and N—H stretch), 2924 and 2851 cm$^{-1}$ (C—H stretch), 1647 cm$^{-1}$ (amide I, C=O stretch), 1541 cm$^{-1}$ (amide II, N—H bend)

Anal. found: C, 53.45; H, 8.02; N, 9.66.

EXAMPLE 9

Process employing a single form of D-glucaric acid, D-glucaro-6,3-lactone to generate activated glucarates suitable for the polymerization to poly(alkyleneglucaramides).

A solution of D-glucaro-6,3-lactone in methanol, (1.92g, 8.4 mmol) and methanolic HCl (3M, 40 mL) was refluxed for three h and then the solvent and residual HCl was removed at reduced pressure. The mixture of activated glucarates was then dissolved in methanol (80 mL) and to this solution was added a methanol solution of hexamethylenediamine, (20.2 mmol) containing triethylamine (1.0 mL). The mixture was stirred at room temperature (48 h), the precipitated polymer removed by filtration, washed with methanol (2×30 mL), and dried at reduced pressure to give the product polymer, poly(hexamethyleneglucaramide, 85% yield, identified by comparison to an authentic sample.

Additional polymers were prepared using the process of the invention and are listed in Table I according to their diacid and diamine monomer units.

TABLE I

POLYMERS PREPARED

| EXAMPLE | ACID MONOMER UNIT (preparation method used) | AMINE MONOMER UNIT (mole ratio) |
|---|---|---|
| 10 | methyl D-glucarate 1,4-lactone (Example 2) | tetramethylenediamine |
| 11 | methyl D-glucarate 1,4-lactone (Example 2) | octamethylenediamine |
| 12 | methyl D-glucarate 1,4-lactone (Example 2) | decamethylenediamine |
| 13 | methyl D-glucarate 1,4-lactone (Example 2) | dodecamethylenediamine |
| 14 | methyl D-glucarate 1,4-lactone (Example 2) | p-xylylenediamine |
| 15 | methyl D-glucarate 1,4-lactone (Example 2) | m-xylylenediamine |
| 16 | methyl D-glucarate 1,4-lactone (Example 2) | 2-methylpentamethylenediamine |
| 17 | methyl D-glucarate 1,4-lactone (Example 2) | 4-azaheptamethylenediamine |
| 18 | ethyl D-glucarate 1,4-lactone (Example 5) | 4-aza-4-methylheptamethylenediamine |
| 19 | ethyl D-glucarate 1,4-lactone (Example 5) | 4-aza-4-methylheptamethylenediamine & polyoxypropylenediamine (0.85:0.15) |
| 20 | ethyl D-glucarate 1,4-lactone (Example 5) | 3,6-dioxaoctamethylenediamine & polyoxypropylenediamine (0.85:0.15) |
| 21 | ethyl D-glucarate 1,4-lactone (Example 5) | 3-azapentamethylenediamine & polyoxypropylenediamine (0.85:0.15) |
| 22 | ethyl D-glucarate 1,4-lactone (Example 5) | 4-aza-4-octadecyheptamethylene-diamine |

Properties of the polymers are shown in Table II below.

TABLE II

| EXAMPLE NO. | NAME | REPEATING STRUCTURAL UNIT | ELEMENTAL ANALYSIS | | | | | | | MP. (°C.) |
|---|---|---|---|---|---|---|---|---|---|---|
| 10 | poly(tetramethylene-D-glucaramide) | $[C_{10}H_{18}N_2O_6]_n$ | CALCD: | C | 45.80 | H | 6.92 | N | 10.68 | 192 (d) |
|  |  |  | FOUND: | C | 45.54 | H | 7.05 | N | 10.60 |  |
| 11 | poly(octamethylene-D-glucaramide) | $[C_{14}H_{26}N_2O_6]_n$ | CALCD: | C | 52.82 | H | 8.23 | N | 8.80 | 195 (d) |
|  |  |  | FOUND: | C | 52.19 | H | 8.35 | N | 8.67 |  |
| 12 | poly(decamethylene-D-glucaramide) | $[C_{16}H_{30}N_2O_6]_n$ | CALCD: | C | 55.47 | H | 8.73 | N | 8.09 | 200 (d) |
|  |  |  | FOUND: | C | 54.90 | H | 8.85 | N | 8.00 |  |
| 13 | poly(dodecamethylene-D-glucaramide) | $[C_{18}H_{34}N_2O_6]_n$ | CALCD: | C | 57.73 | H | 9.15 | N | 7.48 | 200 (d) |
|  |  |  | FOUND: | C | 56.96 | H | 9.25 | N | 7.50 |  |
| 14 | poly(p-xylylene-D-glucaramide) | $[C_{14}N_{18}N_2O_6]_n$ | CALCD: | C | 54.19 | H | 5.85 | N | 9.03 | 200 (d) |
|  |  |  | FOUND: | C | 53.73 | H | 6.15 | N | 8.83 |  |
| 15 | poly(m-xylylene-D-glucaramide) | $[C_{14}H_{18}N_2O_6]_n$ | CALCD: | C | 54.19 | H | 5.85 | N | 9.03 | 210 (d) |
|  |  |  | FOUND: | C | 54.04 | H | 5.94 | N | 8.76 |  |
| 16 | poly(3',6'-dioxaoctamethylene-D-glucaramide | $[C_{12}H_{22}N_2O_8]_n$ | CALCD: | C | 44.72 | H | 6.88 | N | 8.69 | 150 |
|  |  |  | FOUND: | C | 44.05 | H | 6.98 | N | 8.28 |  |
| 17 | poly(2'-methylenepentamethylene-D-glucaramide) | $[C_{12}H_{22}N_2O_6]_n$ | CALCD: | C | 49.65 | H | 7.64 | N | 9.65 | 115 |
|  |  |  | FOUND: | C | 49.23 | H | 7.92 | N | 9.52 |  |
| 18 | poly(4'-aza-heptamethylene-D-glucaramide) | $[C_{12}H_{23}N_3O_6]_n$ | CALCD: | C | 47.20 | H | 7.59 | N | 13.76 | 150 |
|  |  |  | FOUND: | C | 46.42 | H | 7.79 | N | 12.77 |  |
| 19 | poly(4'-aza-4'-methylheptamethylene, polyoxypropylene, D-glucaramide) | $[C_{13}H_{25}N_3O_6]_n$ | CALCD: | C | 48.89 | H | 7.89 | N | 13.16 | 115 |
|  |  |  | FOUND: | C | 47.32 | H | 7.91 | N | 11.82 |  |
| 20 | poly(3',6'-dioxaoctamethylene, polyoxypropylene-D-glucaramide) | $[C_{12}H_{22}N_2O_8]_n$ | CALCD: | C | 44.72 | H | 6.88 | N | 8.69 | 125 |
|  |  |  | FOUND: | C | 44.80 | H | 6.93 | N | 8.67 |  |

TABLE II-continued

| EXAMPLE NO. | NAME | REPEATING STRUCTURAL UNIT | ELEMENTAL ANALYSIS | | | | | | | | MP. (°C.) |
|---|---|---|---|---|---|---|---|---|---|---|---|
| 21 | poly(3',-aza-pentamethylene, polyoxypropylene-D-glucaramide) | $[C_{10}H_{19}N_3O_6]_n$ | CALCD: FOUND: | C C | 43.32 42.85 | H H | 6.91 7.24 | N N | 15.15 14.76 | | 95 |
| 22 | poly(4'-aza-4'-octylheptamethylene-D-glucaramide | $[C_{20}H_{39}N_3O_6]_{10}$ | CALCD: FOUND: | C C | 58.12 58.86 | H H | 9.66 9.81 | N N | 10.35 9.70 | | 130 |

We claim:

1. A one-step process which comprises reacting a salt of glucaric acid selected from the group consisting of sodium, potassium and ammonium salts with a molar excess of a lower aliphatic alcohol in the presence of a strong acid in the substantial absence of water to form at least one glucaric acid ester.

2. The process of claim 1 wherein the strong acid is hydrogen chloride.

3. The process of claim 1 wherein the strong acid is the acid form of an ion exchange resin.

4. The process of claim 1 wherein the salt of glucaric acid is potassium acid glucarate.

5. The process of claim 1 wherein the alcohol is methanol.

6. The process of claim 1 wherein the alcohol is ethanol.

* * * * *